US009844502B2

(12) United States Patent
Vic et al.

(10) Patent No.: US 9,844,502 B2
(45) Date of Patent: Dec. 19, 2017

(54) MAKE-UP COMPOSITION

(71) Applicant: LVMH RECHERCHE, Saint Jean de Braye (FR)

(72) Inventors: Sabine Vic, Semoy (FR); Murielle Farigoule, Checy (FR); Brigitte Noe, Orleans (FR); Eric Perrier, Les Cotes D'Arey (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 14/928,080

(22) Filed: Oct. 30, 2015

(65) Prior Publication Data

US 2016/0045427 A1   Feb. 18, 2016

Related U.S. Application Data

(62) Division of application No. 13/069,100, filed on Mar. 22, 2011, now abandoned.

(30) Foreign Application Priority Data

Mar. 29, 2010  (FR) ..................... 10 52299

(51) Int. Cl.
| | |
|---|---|
| *A61K 8/92* | (2006.01) |
| *A61K 8/81* | (2006.01) |
| *A61K 8/37* | (2006.01) |
| *A61K 8/04* | (2006.01) |
| *A61Q 1/08* | (2006.01) |
| *A61Q 1/02* | (2006.01) |
| *A61K 8/90* | (2006.01) |
| *A61Q 1/12* | (2006.01) |
| *A61Q 1/10* | (2006.01) |
| *A61Q 1/04* | (2006.01) |
| *A61Q 1/06* | (2006.01) |

(52) U.S. Cl.
CPC .............. *A61K 8/922* (2013.01); *A61K 8/042* (2013.01); *A61K 8/37* (2013.01); *A61K 8/8111* (2013.01); *A61K 8/90* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 1/12* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 5,221,534 A | 6/1993 | DesLauriers et al. | |
| 5,945,095 A | 8/1999 | Mougin et al. | |
| 2002/0012682 A1 | 1/2002 | Kashimoto | |
| 2004/0014841 A1 | 1/2004 | Tanaka et al. | |
| 2004/0018219 A1 | 1/2004 | Mateu et al. | |
| 2005/0238603 A1 | 10/2005 | Themens et al. | |
| 2005/0239950 A1 | 10/2005 | Martin et al. | |
| 2009/0142382 A1* | 6/2009 | Shah | A61K 8/26 424/401 |
| 2010/0034767 A1 | 2/2010 | Trabelsi | |

FOREIGN PATENT DOCUMENTS

| | | |
|---|---|---|
| DE | 102 27 409 A1 | 1/2004 |
| DE | 600 23 254 | 8/2006 |
| DE | 603 15 808 T2 | 5/2008 |
| DE | 60 2005 005 0542 | 5/2009 |
| EP | 0 749 746 A1 | 12/1996 |
| EP | 0 923 927 A1 | 6/1999 |
| EP | 0923927 * | 6/1999 |
| EP | 1 584 322 A1 | 10/2005 |
| EP | 1 757 262 A1 | 2/2007 |
| WO | WO 2009/074599 * | 6/2009 |
| WO | WO 2009/075499 | 6/2009 |
| WO | WO 2011/078904 | 6/2011 |

OTHER PUBLICATIONS

English Machine Translation of EP0923927, accessed Sep. 6, 2016.*
French Search Report for corresponding French Patent Application No. 1052299, dated Jan. 3, 2011.

* cited by examiner

*Primary Examiner* — Melissa Fisher
(74) *Attorney, Agent, or Firm* — Merchant & Gould P.C.

(57) ABSTRACT

A make-up composition is for the skin, is prepared by a process and used in a makeup method. The cosmetic composition is intended for making up the skin. The composition has from 75 to 98% by weight of a powder or a mixture of powders, as well as at least one cosmetically acceptable fatty phase having at least one oil. The composition additionally includes a block copolymer of at least one styrene polymer and of at least one olefin polymer, the olefin being other than styrene, or a mixture of these block copolymers.

5 Claims, No Drawings

MAKE-UP COMPOSITION

This application is a Divisional Application of U.S. patent application Ser. No. 13/069,100, filed on 22 Mar. 2011 which claims the benefit of a French Patent Application Serial No. 1052299, filed on 29 Mar. 2010 and which application is incorporated herein by reference. A claim of priority to the extent appropriate is made.

The invention relates to a make-up composition for the skin, to its process of preparation and to a make-up method.

STATE OF THE ART

Make-up for the skin in the form of a powder composition is obviously well known. In addition to loose powders, which are compositions in which the particles forming said powders are not bonded to one another, other powder compositions are known in which the particles forming said powder are bonded to one another to form a pulverulent mass.

In the present patent application, the term "bonded powders" is used to define powder compositions of this second type.

One means for bonding these powder particles to one another can consist of the use of a suitable excipient which performs this role of binder and/or of the use of a process, such as compacting.

A subject-matter of the present invention is compositions in the form of bonded powders.

A major disadvantage of these commercially available compositions results from their excessively high brittleness. This brittleness is generally due to an inadequate cohesion of the powder and is seen in one or more splinters, cracks or other visible damage, for example after a fall. Such a composition, marked after one or more falls, is not satisfactory from the qualitative viewpoint.

PURPOSES OF THE INVENTION

The main purpose of the invention is to solve the technical problem consisting of the provision of a make-up composition for the skin, its process of preparation and a make-up method.

In order to prepare a composition of good quality, the Applicants desire that said composition, once shaped, should withstand several falls. The composition should thus exhibit no splinter, no crack or no other visible damage, after one or more falls from a height of 30 cm.

The powder composition should also exhibit a pleasant feel during the withdrawal of said powder for the operation of making up the skin, and a good hold and satisfactory visual effect after application, and also satisfactory tolerance.

The composition of the invention should, in addition, be prepared with existing industrial equipment and starting materials acceptable from the industrial viewpoint, in particular in cosmetics. Furthermore, it is necessary for the preparation process and the composition itself to be economically and industrially viable and satisfactory. Finally, this must be solved by providing a composition capable of being used as make-up powder for application to the skin.

Thus, it is by attempting to solve these technical problems that the present invention has been brought about.

DESCRIPTION OF THE INVENTION

The present invention relates to a cosmetic composition intended for making up the skin, said composition comprising from 75 to 98% by weight of a powder or a mixture of powders, as well as at least one cosmetically acceptable fatty phase itself comprising at least one oil, said composition being characterized in that it additionally comprises a block copolymer of at least one styrene polymer and of at least one olefin polymer, the olefin being other than styrene, or a mixture of these block copolymers.

The term "comprising" should be understood without implied limitation and opens the possibility of the presence of other compounds, in contrast to the term "consisting".

Preferably, the block copolymer is a diblock or triblock copolymer.

According to a specific embodiment, the olefin polymer of the copolymer comprises, as monomer, an olefin chosen from ethylene, propylene, butylene, butadiene and isoprene.

It is preferable to choose the block copolymer of a styrene polymer and of an olefin polymer, the olefin being other than styrene, from the group consisting of an ethylene/propylene/styrene copolymer, an ethylene/butylene/styrene copolymer, a styrene/butadiene copolymer, an isoprene/styrene copolymer, a styrene/butadiene/styrene copolymer, a styrene/isoprene/styrene copolymer, a styrene/ethylene/butylene/styrene copolymer, or any mixture of the abovementioned copolymers, for example a mixture of ethylene/propylene/styrene and butylene/ethylene/styrene copolymers.

The copolymer can be a partially or completely hydrogenated or non-hydrogenated copolymer.

Preference is given, according to the invention, to an ethylene/propylene/styrene or butylene/ethylene/styrene copolymer or their mixtures, said copolymer advantageously being hydrogenated.

The copolymer preferably exhibits a weight-average molecular weight of from 50,000 to 150,000 g/mol.

The composition advantageously comprises up to 5% by weight of said block copolymer or said mixture of block copolymers, preferably from 0.1 to 2% by weight.

The fatty phase of the composition according to the invention comprises at least one cosmetically acceptable oil.

Within the meaning of the present invention, the term "oil" is understood to mean a compound which is liquid at ambient temperature (25° C.) and atmospheric pressure (1013.25 hPa), and which is insoluble in water or soluble to less than 10% by weight, with respect to the weight of oil introduced into water at 25° C.

The oil is advantageously a non-volatile oil.

The term "non-volatile oil" is understood to mean an oil which exhibits a vapour pressure of less than 0.13 Pa at atmospheric pressure and ambient temperature.

The oil can be chosen from those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or organofluorinated oils, volatile or non-volatile silicone oils, fluorosilicone oils and their mixtures.

Mention is made, as example of oils of animal, vegetable or mineral origin, of lanolin, squalene, fish oil, perhydrosqualene, mink oil, turtle oil, soybean oil, grape seed oil, sesame oil, maize oil, rapeseed oil, sunflower oil, cottonseed oil, avocado oil, olive oil, castor seed oil, jojoba seed oil, peanut oil, sweet almond oil, palm oil, cucumber oil, hazelnut oil, apricot kernel oil, wheat germ oil, calophyllum oil, macadamia oil, coconut oil, cereal germ oil, candlenut oil, thistle oil, candelilla oil, safflower oil, shea butter, and their mixtures.

Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

Mention is made, as examples of optionally branched and/or unsaturated fatty acids, of myristic acid, palmitic acid, stearic acid, behenic acid, oleic acid, linoleic acid, linolenic acid or isostearic acid, and their mixtures.

Mention is made, as example of optionally branched and/or unsaturated fatty alcohols, of cetanol, stearyl alcohol, oleyl alcohol, cetyl alcohol, octyldodecanol, and their mixtures.

Mention is made, as examples of esters, of monoesters or polyesters of fatty acids, the linear or branched fatty chain of which includes from 6 to 30 carbon atoms, and of fatty alcohols, the fatty chain of which includes from 3 to 30 carbon atoms, in particular mono- and polyesters of hydroxy acids and of fatty alcohols, esters of benzoic acid and of fatty alcohols, polyesters of polyols, dipentaerythrityl $C_5$-$C_9$ esters, polyesters of polyglycerol, trimethylolpropane polyesters, propylene glycol polyesters, polyesters of hydrogenated castor oil, and more particularly isononyl isononanoate, stearyl octanoate, isopropyl palmitate, isopropyl myristate, butyl stearate, hexyl laurate, 2-ethylhexyl palmitate, 2-hexyldecyl laurate, 2-octyldecyl palmitate, 2-octyldodecyl myristate, di(2-ethylhexyl) succinate, diisostearyl malate, 2-octyldodecyl lactate, glyceryl triisostearate or diglyceryl triisostearate, octyldodecyl stearoyl stearate (Ceraphyl), cetearyl isononanoate, diisopropyl adipate, caprylic/capric triglyceride, glyceryl tricaprate/caprylate, isocetyl stearoyl stearate, $C_{12}$-$C_{15}$ alkyl benzoates, pentaerythrityl tetraisostearate, dipentaerythrityl pentaisononanoate, bis-diglyceryl polyacyladipate-2, trimethylolpropane triethylhexanoate, propylene glycol dibenzoate, propylene glycol dioctanoate, and their mixtures.

Mention is made, as example of volatile silicone oils, of hexamethyldisiloxane, dimethicones with a viscosity of between 0.65 and 5 mm$^2$/s, octamethylcyclotetrasiloxane, heptamethylhexyltrisiloxane, decamethylcyclopentasiloxane, decamethyltetrasiloxane, octamethyltrisiloxane, dodecamethylcyclohexasiloxane, heptamethyloctyltrisiloxane, and their mixtures.

Mention is made, as example of non-volatile silicone oils, of non-volatile polydialkylsiloxanes; polydimethylsiloxanes comprising pendant alkyl, alkoxy or phenyl groups or alkyl, alkoxy or phenyl groups at the end of the silicone chain, which groups have from 2 to 24 carbon atoms; phenylated silicones, such as those of the phenyl trimethicone type, those of the phenylpropyldimethylsiloxysilicate type or those of the trimethylpentaphenyltrisiloxane type; polysiloxanes modified by fatty acids, in particular $C_8$-$C_{20}$ fatty acids, fatty alcohols, in particular $C_8$-$C_{20}$ fatty alcohols, or polyoxyalkylenes (in particular polyoxyethylene and/or polyoxypropylene); aminated polysiloxanes; polysiloxanes comprising a hydroxyl group; and their mixtures.

Mention is made, as fluorosilicone oils, of fluorinated polysiloxanes comprising a pendant fluorinated group or a fluorinated group at the end of the silicone chain having from 1 to 12 carbon atoms, all or a portion of the hydrogens of which are replaced by fluorine atoms, such as perfluorononyl dimethicone, and their mixtures.

It is understood that, within the meaning of the invention, the choice may be made of an oil belonging to one of the families mentioned above, or an oil from those listed above, or a mixture of at least two of these oils.

It is also possible advantageously to choose a glossy oil, that is to say an oil exhibiting a refractive index of greater than 1.45 and preferably of greater than 1.47.

According to a preferred embodiment of the invention, the choice is made of at least one oil from hydrogenated polyisobutene, isononyl isononanoate or a jojoba seed oil.

The oil can constitute up to 100% of the fatty phase, and advantageously constitutes more than 85% by weight of the fatty phase.

In addition to at least one oil, the fatty phase of the composition according to the invention can comprise one or more other fatty substances chosen by a person skilled in the art on the basis of his general knowledge, so as to confer the desired properties, for example, of consistency and/or texture, on the final composition.

These additional fatty substances can advantageously be chosen from waxes or pasty fatty substances.

These additional fatty substances can be of animal, vegetable, mineral or synthetic origin.

The term "wax" is understood to mean a fatty substance which exhibits a reversible liquid/solid change in state, which has a melting point of greater than 30° C. and generally of less than 90° C., and which exhibits, in the solid state, an anisotropic crystalline arrangement.

The waxes used according to the invention can be composed of polar or nonpolar waxes or a mixture of both. The term "nonpolar" is understood to mean a wax which includes only carbon, hydrogen and/or phosphorus atoms and in particular a hydrocarbon.

Mention is made, as example of waxes, of microcrystalline waxes, ozokerite, beeswax (Cera alba), candelilla, carnauba or Japan waxes, paraffin, polymethylene, polyethylene, polypropylene or ethylene/propylene copolymer waxes, and their mixtures, animal waxes, vegetable waxes and synthetic or silicone waxes including polar groups, such as esters, ouricury waxes, Chinese insect (Ericerus pela) waxes; sumac or montan waxes, cocoa butter, cork fibre waxes, triesters of $C_8$-$C_{20}$ acids and of glycerol, such as glyceryl tribehenate, acetylated glycol stearate, and their mixtures.

These waxes can be used in particular in the form predispersed in an oil, as is the case with the mixture of candelilla waxes and of jojoba seed oil.

The fatty phase advantageously comprises up to 7%, by weight of the composition, of a wax, preferably up to 5% by weight.

The fatty phase of the composition of the invention can also comprise one or more pasty fatty substances (or pasty agents) of animal, vegetable, mineral or synthetic origin, and their mixtures.

The term "pasty fatty substances" or "pasty agent" is understood to mean, within the meaning of the present invention, a lipophilic fatty compound which exhibits a reversible solid/liquid change in state, which exhibits, in the solid state, an anisotropic crystalline arrangement and which comprises, at a temperature of 23° C., a liquid fraction and a solid fraction.

In other words, the starting melting point of the pasty compound can be less than 23° C. The liquid fraction of the pasty compound, measured at 23° C. can represent up to 95% by weight of the compound, preferably between 15 and 85% by weight.

The pasty fatty substance can advantageously be chosen from polymeric or non-polymeric silicone compounds, polymeric or non-polymeric fluorinated compounds, vinyl polymers, olefin homopolymers or copolymers, hydrogenated diene homopolymers and copolymers, linear or branched and homo- or copolymeric oligomers of alkyl (meth)acrylates preferably having a $C_8$-$C_{30}$ alkyl group, homo- and copolymeric oligomers of vinyl esters having $C_8$-$C_{30}$ alkyl groups, homo- and copolymeric oligomers of vinyl ethers having $C_8$-$C_{30}$ alkyl groups, fat-soluble polyethers resulting from polyetherification between one or more $C_2$-$C_{100}$ diols, preferably $C_2$-$C_{50}$ diols, esters, and their mixtures.

Mention is made, among esters, of esters of an oligomeric glycerol, in particular esters of diglycerol, especially condensates of adipic acid and of glycerol, for which a portion of the hydroxyl groups have reacted with a mixture of fatty acids, such as stearic acid, capric acid, isostearic acid and 12-hydroxystearic acid, phytosterol esters, arachidyl propionate, triglycerides of fatty acids and their derivatives, pentaerythritol esters, non-crosslinked polyesters resulting from the polycondensation between a linear or branched $C_4$-$C_{50}$ dicarboxylic acid or polycarboxylic acid and a $C_2$-$C_{50}$ diol or polyol, aliphatic esters resulting from the esterification of an aliphatic hydroxycarboxylic acid ester by an aliphatic carboxylic acid, polyesters resulting from esterification by a polycarboxylic acid of an aliphatic hydroxycarboxylic acid ester, said ester comprising at least two hydroxyl groups, esters of dimer diol and dimer diacid, if appropriate esterified on their free alcohol or acid functional group(s) by acid or alcohol radicals, and their mixtures.

Mention may be made, as pasty compounds of vegetable origin, of a mixture of sterols of soybean and of polyoxyethylenated (5 EO)/polyoxypropylenated (5 PO) pentaerythritol.

A preferred pasty substance is an ester of dimer diol and dimer diacid and more particularly that having the INCI name Bis-Behenyl/Isostearyl/Phytosteryl Dimer Dilinoleyl Dimer Dilinoleate, or a phytosterol ester synthesized from vegetable matter and sold under the trade name Plandool® G.

The fatty phase advantageously comprises up to 7%, by weight of the composition, of a pasty agent, advantageously up to 5% by weight.

The powder or the mixture of powders comprises those which are known and normally used in the preparation of cosmetic compositions, in particular in the preparation of make-up cosmetic compositions.

Said powder or said mixture of powders comprises or is composed of a colouring agent.

Said colouring agent can thus optionally represent up to 98% by weight of the composition.

Said colouring agent itself comprises at least one pigment and advantageously at least one filler, said colouring agent advantageously being composed of a mixture of at least one pigment and of at least one filler.

The pigments can be chosen from inorganic pigments, organic pigments and pearlescent pigments.

Mention may be made, among inorganic pigments, as examples, of titanium dioxide (rutile or anatase), optionally surface-treated; black, yellow, red and brown iron oxides, manganese violet; ultramarine blue, chromium oxide, hydrated chromium oxide and ferric blue.

Mention may be made, among organic pigments, for example of the pigments D & C Red No. 19, D & C Red No. 9, D & C Red No. 21, D & C Orange No. 4, D & C Orange No. 5, D & C Red No. 27, D & C Red No. 13, D & C Red No. 7, D & C Red No. 6, D & C Yellow No. 5, D & C Red No. 36, D & C Orange No. 10, D & C Yellow No. 6, D & C Red No. 30, D & C Red No. 3, carbon black and lakes based on cochineal carmine.

The pearlescent pigments can be chosen in particular from white pearlescent pigments, such as mica covered with titanium oxide or bismuth oxychloride, and coloured pearlescent pigments, such as titanium oxide-coated mica with iron oxides, titanium oxide-coated mica with ferric blue or chromium oxide, titanium oxide-coated mica with an organic pigment of the abovementioned type, and pigments based on bismuth oxychloride.

The pigments may advantageously constitute up to 90% by weight of the colouring agent, preferably from 75 to 85% by weight of the colouring agent, the balance being composed of the fillers.

The fillers are chosen in particular from talc, which is a hydrated magnesium silicate and which is advantageously provided in the form of particles generally with dimensions of less than 40 µm; micas, which are aluminosilicates with varied compositions and which are advantageously provided in the form of flakes having dimensions of from 2 to 200 µm, preferably of from 5 to 70 µm and a thickness of from 0.1 to 5 µm, preferably of from 0.2 to 3 µm; micas of natural origin (for example muscovite, margarite, roscoelite, lepidolite, biotite) or of synthetic origin; kaolin, which is a hydrated aluminium silicate and which is advantageously provided in the form of lamellar particles having dimensions generally of less than 30 µm; zinc and titanium oxides; precipitated calcium carbonate, advantageously in the form of particles with dimensions of less than 10 µm, magnesium carbonate and basic magnesium carbonate; silica; or metal soaps derived from organic carboxylic acids having from 8 to 22 carbon atoms, preferably from 12 to 18 carbon atoms, for example zinc stearate, magnesium stearate, lithium stearate, zinc laurate or magnesium myristate; these soaps advantageously being in the form of particles having dimensions of less than 10 µm.

Use may also be made of powders formed of nonexpanded synthetic polymers, such as polyethylene, polyesters (for example polyethylene isophthalate or terephthalate) and polyamides (for example Nylon™); inorganic powders such as spherical silica; spherical titanium dioxides; glass and ceramic beads; powders formed of organic materials of natural origin, such as crosslinked or non-crosslinked maize, wheat, or rice starches; powders formed from crosslinked or non-crosslinked and optionally spheronized synthetic polymers, such as polyamide powders, for example poly(β-alanine) powders and nylon powders, powders formed of polyacrylic or polymethacrylic acids, polystyrene powders crosslinked by divinylbenzene, silicone resin powders or Teflon™ powders.

As results from the above list, the filler can comprise a "non-compactable" filler which can comprise, in particular
    solid microspheres, made of any organic or inorganic material compatible with use on the skin, that is to say non-irritating and non-toxic. These microspheres can be microporous, in which case they have a specific surface of at least 0.5 $m^2/g$, and can optionally be impregnated, in particular with cosmetically active agents or excipients.
    hollow microspheres, made of thermoplastic material and prepared by known processes, in particular made of polymers or copolymers of ethylenic derivatives, of polyamides, of polyesters, of urea-formaldehyde polymers or of vinylidene chloride copolymers,
    microcapsules, made of organic or inorganic material compatible with use on the skin and which can optionally include a cosmetically active agent or an excipient. The polymeric microcapsules can be made from, in particular, polymers or copolymers derived from monomeric acids, amines, or esters possessing ethylenic unsaturation, of urea-formaldehyde polymers, or of vinylidene chloride polymers or copolymers, some lamellar fillers and in particular titanium oxide-coated micas, some sericites and some talcs.

According to one alternative embodiment of the invention, use may be made of powders which have been treated beforehand so as to modify the shape and/or surface state of the particles constituting said powders and/or so as to modify the visual and/or sensory properties thereof, and/or so as to modify the behaviour thereof, in particular during the preparation of the cosmetic compositions in which these treated powders are employed. This treatment is applied more particularly to the pigments and to the fillers which can be used in the preparation of the invention, it being understood that the composition can comprise, without distinction, treated or untreated powders.

The treatment of these powders can consist of a partial or complete coating of the particles of these powders using substances such as amino acids, silicones, such as dimethicone, metal salts or collagen.

The solid particles forming the powder advantageously have a mean diameter of greater than 100 nm and up to 200 µm, and more particularly a diameter of between 10 and 100 µm.

It is also possible to include, in a powder mixture which can be used for the invention, a powder fraction having particles of a mean diameter of between 1 nm and 100 nm.

The composition according to the invention can additionally comprise adjuvants which can be chosen in particular from UV-A or UV-B sunscreens, preservatives, antioxidants, fragrances, and one or more cosmetically active agents.

These active agents can be of natural or synthetic origin and are provided in particular in the form of a plant or plant part extract or extract solution or of a molecule which is synthesized or isolated from one of these extracts.

The plant extract can be obtained from any cosmetically acceptable extraction process and in particular by an extraction process employing a polar solvent or mixture of polar solvents which can be chosen from water, alcohols comprising from 1 to 6 carbon atoms, or alternatively glycols.

The make-up composition according to the present invention is advantageously presented in the form of a blusher, eye shadow, foundation, make-up base, gloss or anhydrous lip product.

The present invention is not particularly limited in the compounds which it comprises. However, it is necessary for these compounds to be acceptable topically, that is to say suitable for being brought into contact with the human skin without toxicity, incompatibility, allergic response or equivalents going beyond acceptable qualitative and/or quantitative tolerances. This bringing into contact with the surface of the skin is carried out directly or indirectly and generally by simple topical application.

As explained above, the composition of the invention which can be used for making-up is sufficiently resistant to withstand at least three falls from a height of 30 cm, without exhibiting the least splinter or crack or other visible damage.

The invention also relates to a pulverulent mass comprising from 75 to 98% by weight of a powder or a mixture of powders, with respect to the weight of the total pulverulent mass, and at least one cosmetically acceptable fatty phase, said fatty phase having at least one oil, said composition being characterized in that it additionally comprises a block copolymer of at least one styrene polymer and at least one olefin polymer, the olefin being other than styrene, or a mixture of these block copolymers. This pulverulent mass makes possible in particular the preparation of the cosmetic composition of the invention. All the embodiments and alternative forms relating to the composition are thus applicable to it.

The block copolymer of styrene and of olefin other than styrene and the fatty phase comprising at least one oil advantageously form a lipophilic gel.

According to a particularly preferred embodiment of the invention, the block copolymer as defined above or a mixture of these block copolymers, is advantageously dispersed in the fatty phase such as to form a lipophilic gel.

This lipophilic gel is advantageously used as binding agent for the powder.

According to a preferred embodiment, the lipophilic gel advantageously comprises up to 20% by weight of a block copolymer as defined above or of a mixture of these block copolymers, preferably from 1 to 10% by weight.

The lipophilic gel itself advantageously represents from 2 to 25% by weight of the composition, preferably between 10 and 20% by weight.

Another subject-matter of the invention relates to a process for the preparation of the composition according to the invention.

The process is in particular characterized in that it comprises the following steps:
a step of preparation of a powder or a mixture of powders,
a step of preparation of a lipophilic gel formed by dispersion of an abovementioned block copolymer or of a mixture of these block copolymers in at least one fatty phase comprising an oil,
a step of bringing the powder into contact with said lipophilic gel in order to bind the particles of said powder and to form a homogeneous pulverulent mass,
a step of shaping the pulverulent mass obtained above.

The pulverulent mass is obtained by a manufacturing process as described above in the absence of the shaping step.

The shaping is advantageously carried out by compacting, by extrusion or else by casting, followed by suction.

The preparation of the powder employed in the process of the invention can in particular comprise a step of mixing the various powders or pulverulent materials employed, so as to obtain a homogeneous mixture and a step of milling and/or of micronizing said powder so as to reduce the mean size of the particles and to reduce the difference in size between the various components of the powder mixture.

The step of formation of the lipophilic gel comprises a step of bringing the polymer into contact with the fatty phase as defined above, which is used as dispersing agent for said polymer, and then a mixing step in order to render said dispersion homogeneous.

According to a particularly preferred implementation of the process of the invention, use is made of a commercially available gel in which the copolymer or copolymer mixture is dispersed beforehand in an oil.

When a commercial gel is employed, it can advantageously be diluted, so as to reduce the viscosity thereof, with the same oil as the dispersing agent of the commercial product or else with a different but compatible oil.

The step of formation of the gel can comprise diluting the gel with an oil, so as to reduce the viscosity thereof, preferably with the same oil as the dispersing agent for the copolymer.

During this step, other compounds, such as a wax or a pasty agent or also adjuvants, can be included in said dispersion.

The shaping step can be carried out by any type of process known to a person skilled in the art.

The shaping can be carried out in particular by compacting or by casting, followed by suction.

Before compacting, the pulverulent mass is sieved beforehand.

The pulverulent mass is compacted in a pot. This pot is composed of a material compatible with the composition and of any shape.

The compacting force is suitable for the composition, so that the compacted composition can be used for making up and is sufficiently resistant to withstand at least three falls from a height of 30 cm, without exhibiting the least splinter or crack or other visible damage.

According to an alternative form of the invention, the composition can be shaped by casting the pulverulent mass over a sheet or in a pot.

The sheet can, for example, be a microporous ceramic sheet.

The casting is advantageously supplemented by a step of sucking off the air present in the pulverulent mass, so as to extract the residual air therefrom and to improve the cohesion of the mixture.

In the case of a shaping by casting, use may be made of a wetting agent during the step of preparation of the powder or during the step of bringing the powder into contact with the abovementioned lipophilic gel.

The wetting agent makes it possible to improve the cohesion of the pulverulent mass during the casting step.

The wetting agent is an agent which is volatile under the conditions of the step of shaping the powder, so that it is completely removed from the composition. It can be removed at ambient temperature or else by heating.

The process can comprise in particular a drying step, in order to remove any trace of a volatile compound, and/or a cooking step, said step succeeding the step of shaping the pulverulent mass. In the case where the preparation process requires a cooking step, the pulverulent mass is advantageously cast over a ceramic sheet which withstands the cooking temperatures.

The shaping can also be carried out by extrusion, under cold conditions or else under hot conditions.

Another subject-matter of the invention is targeted at the use of a lipophilic gel comprising a copolymer as mentioned above, to prepare a composition itself comprising from 75 to 98% by weight of the composition, of a powder or of a powder mixture.

Another subject-matter of the invention relates to a make-up method comprising the application, to the skin, of a composition of the invention. In particular, the method of the invention comprises the application of a composition of the invention to at least a part of the skin of the face, preferably by withdrawing with a tool or a device suitable for the withdrawing of a powder, such as brushes, including fine brushes, powder puffs, foam applicators or sponges.

Other aims, characteristics and advantages of the invention will become clearly apparent to a person skilled in the art subsequent to reading the explanatory description, which refers to examples which are given solely by way of illustration and which cannot in any way limit the scope of the invention.

The examples form an integral part of the present invention and any characteristic which, starting from the description taken in its entirety, including the examples, appears novel with respect to any prior state of the art forms an integral part of the invention in its function and in its general nature.

Thus, each example has a general scope.

Moreover, in the examples, all the percentages are given by weight, unless otherwise indicated, the temperature is expressed in degrees Celsius, unless otherwise indicated, and the pressure is atmospheric pressure, unless otherwise indicated.

EXAMPLES

Make-Up Compositions According to the Invention

Example 1

Compact Powder—Matt Formulations

Composition 1A (% by Weight of the Composition)

| Phase A (powders) | |
|---|---|
| Dimethicone-treated talc | 19.5 |
| Dimethicone-treated mica | 50 |
| Magnesium stearate | 2 |
| Calcium sodium borosilicate | 0.5 |
| Sorbic acid | 0.1 |
| Pigments | 12.2 |
| Phase B | |
| 1,2-Pentanediol | 1 |
| 1,2-Octanediol | 0.2 |
| Plandool ® G | 0.5 |
| Isononyl isononanoate | 12.6 |
| Ethylene/propylene/styrene hydrogenated copolymer | 0.4 |
| Butylene/ethylene/styrene hydrogenated copolymer | 1.0 |
| Preservatives | <0.1 |

PLANDOOL ® G, INCI = Bis-behenyl/isostearyl/phytosteryl dimer dilinoleyl dimer dilinoleate.

Example 2

Compact Power—Pearlescent Formulations

Composition 2A (% by Weight of the Composition)

| Phase A (powders) | |
|---|---|
| Dimethicone-treated talc | 16.5 |
| Nylon 12 | 3 |
| Magnesium stearate | 2 |
| Calcium sodium borosilicate | 0.5 |
| Sorbic acid | 0.1 |
| Pigments | 12.2 |
| Pearlescent agents | 50 |
| Phase B | |
| Ethylene/propylene/styrene hydrogenated copolymer | 0.6 |
| Butylene/ethylene/styrene hydrogenated copolymer | 0.1 |
| Phenoxyethanol | 0.7 |
| Plandool ® G | 0.5 |
| Jojoba oil | 13.3 |

Composition 2B (% by Weight of the Composition)

| Phase A (powders) | |
|---|---|
| Dimethicone-treated talc | 16.5 |
| Nylon 12 | 3 |

-continued

| | |
|---|---|
| Magnesium stearate | 2 |
| Calcium sodium borosilicate | 0.5 |
| Sorbic acid | 0.1 |
| Pigments | 12.2 |
| Pearlescent agents | 50 |
| Phase B | |
| Hydrogenated polyisobutene | 13.2 |
| Phenoxyethanol | 0.7 |
| Plandool ® G | 0.5 |
| Ethylene/propylene/styrene copolymer | 0.4 |
| Butylene/ethylene/styrene copolymer | 0.4 |

Composition 2C (% by Weight of the Composition)

| | |
|---|---|
| Phase A (powders) | |
| Dimethicone-treated talc | 16.5 |
| Nylon 12 | 3 |
| Magnesium stearate | 2 |
| Calcium sodium borosilicate | 0.5 |
| Sorbic acid | 0.1 |
| Pigments | 12.2 |
| Pearlescent agents | 50 |
| Phase B | |
| Jojoba oil | 6.5 |
| 1,2-Pentanediol | 1 |
| 1,2-Octanediol | 0.2 |
| Plandool ® G | 0.5 |
| Ethylene/propylene/styrene copolymer | 0.3 |
| Butylene/ethylene/styrene copolymer | 0.2 |
| Octyldodecyl stearoyl stearate | 7 |

Example 3

Compact Powder—Glitter Formulations

Composition 3A (% by Weight of the Composition)

| | |
|---|---|
| Phase A (powders) | |
| Dimethicone-treated talc | 19.5 |
| Magnesium stearate | 2 |
| Calcium sodium borosilicate | 0.5 |
| Sorbic acid | 0.1 |
| Pigments | 12.2 |
| Pearlescent agents | 50 |
| Phase B | |
| 1,2-Pentanediol | 1 |
| 1,2-Octanediol | 0.2 |
| Plandool ® G | 0.5 |
| Isononyl isononanoate | 12.6 |
| Ethylene/propylene/styrene copolymer | 1.1 |
| Butylene/ethylene/styrene copolymer | 0.3 |

The Formulations are Obtained According to the Following Process:

A laboratory mixer (Lödige) is used in order to homogenize and disperse the various constituents of the formulation.

The excipients and pigments of the phase A are weighed out and then dispersed with the mixer.

The pearlescent agents are added to the preceding mixture and dispersing is carried out at slow speed.

The compounds of the phase B are heated to 50° C., which is subsequently added very gradually to the mixture obtained in the preceding step, with a step of dispersion and then of homogenization at high speed. It is optionally possible to alternate the addition of a portion of the powder and then a portion of the phase B, in order to facilitate the preparation of a homogeneous pulverulent mass.

The homogeneous pulverulent mass is recovered and then placed in a suitable support. It is subsequently covered with a compacting cloth before the compaction step proper, carried out using a manual compacting device.

The compacting force is adjusted manually and is between 50 and 150 bar, in order to obtain a powder compact which is satisfactory from a visual viewpoint, the cohesion of which is sufficient to withstand the fall test mentioned in the description.

The compositions presented in Examples 1 to 3 are eyeshadows, which are withdrawn in order to be applied to the skin in order to obtain a make-up effect.

In particular, they exhibit a feel and a texture which are surprising and particularly pleasant at the time of the withdrawal of the product.

It is entirely possible to use them as cosmetic compositions intended for making up the skin.

The invention claimed is:

1. A method for preparing a make-up composition selected from the group consisting of a blusher, an eye shadow, a foundation, and a make-up base, the method comprising:
   preparing a mixture of powders comprising at least one dimethicone-treated filler and at least one pigment;
   mixing the mixture of powders with a lipophilic gel comprising a mixture of ethylene/propylene/styrene and butylene/ethylene/styrene copolymers dispersed in a fatty phase comprising a non-volatile oil selected from the group consisting of hydrogenated polyisobutene, isononyl isononanoate, and jojoba seed oil into a homogenous pulverulent mass comprising 75 to 98% of the mixture of powders by weight of the composition;
   compacting the homogenous pulverulent mass with a compacting force between 50 and 150 bar to prepare a compacted bonded powder,
   wherein the make-up composition comprises 0.5 to 1.4% by weight of the mixture of ethylene/propylene/styrene and butylene/ethylene/styrene copolymers.

2. The method of claim 1, wherein the mixture of ethylene/propylene/styrene and butylene/ethylene/styrene copolymers are partially hydrogenated.

3. The method of claim 1, wherein the mixture of ethylene/propylene/styrene and butylene/ethylene/styrene copolymers are hydrogenated.

4. The method of claim 1, wherein the mixture of ethylene/propylene/styrene and butylene/ethylene/styrene copolymers are non-hydrogenated.

5. The method of claim 1, wherein the composition comprises at least one of adjuvants, preservatives, antioxidants, fragrances, and cosmetically active agents.

* * * * *